United States Patent [19]

Iguchi et al.

[11] Patent Number: 5,013,734
[45] Date of Patent: May 7, 1991

[54] NOVEL ESTERS OF PHENYLALKANOIC ACID

[75] Inventors: Sadahiko Iguchi; Masanori Kawamura; Tsumoru Miyamoto, all of Osaka, Japan

[73] Assignee: Ono Pharmaceutical Co., Ltd., Osaka, Japan

[21] Appl. No.: 521,962

[22] Filed: May 11, 1990

[30] Foreign Application Priority Data

May 12, 1989 [JP] Japan .................................. 1-119873

[51] Int. Cl.$^5$ .................. A61K 31/535; C07D 317/22; C07D 295/073; C07D 233/02
[52] U.S. Cl. .................. 514/231.5; 514/255; 514/336; 514/467; 544/149; 544/151; 544/374; 544/375; 546/270; 546/283; 549/441; 549/448; 549/452
[58] Field of Search .................. 549/441, 448, 452; 544/149, 151, 374, 375; 546/270, 283; 514/231.5, 255, 336, 467

[56] References Cited

U.S. PATENT DOCUMENTS 4,548,941 10/1985 Halczenko et al. .................. 514/295

FOREIGN PATENT DOCUMENTS 041491 12/1981 European Pat. Off. .
0093155 8/1986 European Pat. Off. .
83/01772 5/1983 PCT Int'l Appl. .
2169892 7/1986 United Kingdom .

OTHER PUBLICATIONS

Chemical Abstracts, vol. 67, No. 25, Dec. 18, 1967, "Cardiovascular Effects of 1,3-Dioxolanes", p. 10876, col. 2, Abstract No. 115 561j.
Chemical Abstracts, vol. 75, No. 1, Jul. 5, 1971, John Hidalgo et al., "Etoxadrol (CL-1848C) (d-2-ethyl-2-phenyl-4-(2-piperidyl)-(1,3-dioxolane hydrochloride)) a New Dissociative Anesthetic . . .".
Chemical Abstracts, vol. 98, Mar. 28, 1983, No. 13, Dr. Karl Thomae, GMBH, "Phenylalkylamines and Their Use as Medicines", p. 569, col. 2, Abstract-No. 106 947c and Kokai-No.
Chemical Abstracts, vol. 88, Mar. 27, 1978, No. 13, Tasaburo Kiguchi et al., "p-alkoxyphenyl Lower Fatty Acid Derivatives", p. 493, col. 2, Abstract No. -89 384r and Japan, Kokai 77, 131, 552.

Primary Examiner—Mary C. Lee
Assistant Examiner—Peter Davis

Attorney, Agent, or Firm—Sughrue, Mion, Zinn, Macpeak & Seas

[57] ABSTRACT

The esters of phenylalkanoic acid of the formula:

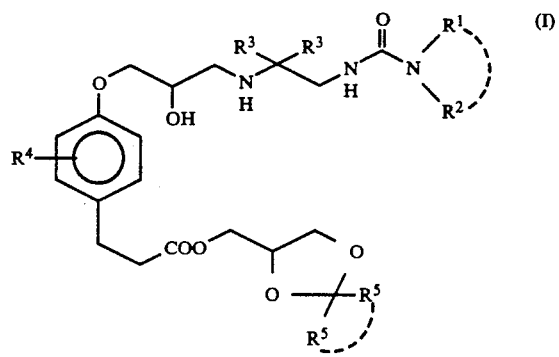

wherein
$R^1$ is 4–10 membered, saturated or unsaturated, mono- or bi-cyclic hetero ring containing as hetero atoms:
 (i) one or two nitrogen,
 (ii) two or three of nitrogen and sulfur in total, or
 (iii) one or two sulfur;
$R^2$ is hydrogen; or
$R^1$ and $R^2$, taken together with a nitrogen to which they are attached, form 4–7 membered, saturated or unsaturated, mono-cyclic hetero ring containing as hetero atoms:
 (i) one or two nitrogen, or
 (ii) two or three of nitrogen and oxygen in total,
the aforementioned hetero rings, represented by $R^1$ or formed by $R^1$ and $R^2$, taken together with a nitrogen to which they are attached, may be substituted by one substituent selected from C1–4 alkyl and C2–5 acyl;
$R^3$ each, independently, is hydrogen or C1–4 alkyl;
$R^4$ is hydrogen, halogen, trihalomethyl, C1–4 alkyl, C1–4 alkoxy, C2–5 acyl, cyano, nitro or nitroxy;
$R^5$ each, independently, is hydrogen, C1–4 alkyl or phenyl; or the two $R^5$'s, taken together with a carbon to which they are attached, form cyclopentane or cyclohexane;

and the pharmaceutically acceptable acid addition salts thereof, have $\beta_1$-adrenergic receptor blocking activity, and therefore, are useful for the prevention of and/or in the treatment of cardiovascular diseases such as angina pectoris, myocardial infarction, congestive heart failure, hypertension, arrhythmia, etc.

9 Claims, No Drawings

NOVEL ESTERS OF PHENYLALKANOIC ACID

FIELD OF THE INVENTION

The present invention relates to novel esters of phenylalkanoic acid. More particularly, this invention relates to:

(i) esters of phenylalkanoic acid of the following formula:

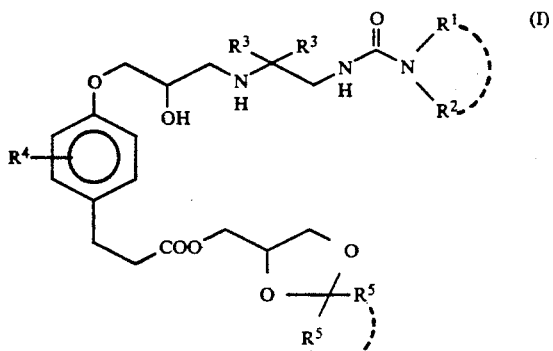

wherein all of the symbols are the same meanings as described hereinafter, and the pharmaceutically acceptable acid addition salts thereof, which have $\beta_1$-adrenergic receptor blocking activity, (ii) processes for the preparation thereof, and (iii) $\beta_1$-adrenergic receptor blocking agents containing them.

BACKGROUND OF THE INVENTION

On the surface of cellular tissue responding to the stimulation of sympathetic nerve, the adrenergic receptor exists. This receptor is divided into two types, i.e. $\alpha$ and $\beta$. The reaction via $\alpha$-receptor is generally excitation, and causes the contraction of a smooth muscle and vessel.

On the other hand, the response of heart caused by the stimulation of $\beta_1$-receptor is the excitation such as the increase of heart rate, contraction and automaticity. The stimulation of $\beta_2$-receptor causes the relaxation of smooth muscle, e.g. tracheal, intestinal, uterine smooth muscle, etc. and the dilation of vessel.

Accordingly, the selective blockade of $\beta_1$-receptor acts on the heart depressedly, and gives physiological changes, for example, the decrease of heart rate, contraction, automaticity and stroke volume. Such pharmacological properties show that $\beta_1$-receptor blockers are useful for the treatment of diseases which need the utmost decrease of myocardial oxygen demand, i.e. angina pectoris, myocardial infarction, congestive heart failure, hypertension, arrhythmia, etc.

RELATED ARTS

Up until now, the various $\beta_1$-blocking agents have been developed in order to accomplish the purpose described hereinbefore. Most of these agents have 3-aryloxy-2-hydroxypropylamine as the basic skeleton, and some of them have been already produced commercially.

Recently, the derivatives having a high selectivity for $\beta_1$-receptor and having a short duration, have been energetically developed.

The reason is because the conventional $\beta_1$-blockers block $\beta_2$-receptor slightly, as well as block $\beta_1$-receptor, and therefore induce occasionally the increase of broncho-resistance and thus bronchial asthma.

The short-acting blockers are characterized by the ability to easily control the effect of the treatment. For example, the administration of $\beta_1$-blocker to a patient in acute myocardial infarction induces the decrease in myocardial oxygen demand and the prevention of the magnification of infarct area, and therefore is very useful. However, if $\beta_1$-blocking effect should continue after recovering the symptom, the function of heart would be excessively inhibited and his life would be endangered. In such case, it is desirable to remove the $\beta_1$-blocking effect soon.

For example, there are known some short-acting derivatives having highly selective $\beta_1$-receptor blocking activity, as follows.

(1) in the specification of the European Patent Publication No. 41491, the compounds of the formula:

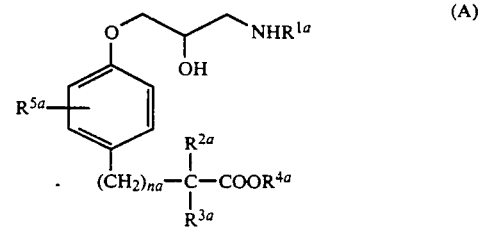

wherein $R^{1a}$ is a group selected from isopropyl and tert-butyl;

$R^{2a}$ and $R^{3a}$, independently, are hydrogen;

$R^{5a}$ is a group selected from hydrogen, halogen, lower alkyl, lower alkenyl and lower alkoxy;

$R^{4a}$ is a group selected from alkyl, alkoxyalkyl, cycloalkyl, phenyl, arylakyl and hydroxyalkyl; and na is 1 or 2, are disclosed, and (2) in the specification of the European Patent Publication No. 93155, the compounds of the formula:

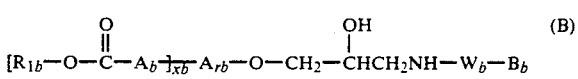

wherein $R_{1b}$ is lower alkyl, lower cycloalkyl, lower alkenyl, lower alkynyl, lower alkycarboxymethyl, arylcarboxymethyl, aryl or aralkyl;

$A_b$ is bond, lower alkylene or lower alkenylene;

$X_b$ is 1 or 2, with the proviso that when $X_b$ is more than 1, each of

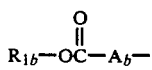

may be the same or different;

$A_{rb}$ is a heterocyclic ring, unsubstituted aromatic ring, or aromatic ring substituted by lower alkyl, lower alkenyl, lower alkynyl, lower alkoxy, halogen, acetoamido, amino, nitro, lower alkylamino, hydroxy, lower hydroxyalkyl or cyano;

$W_b$ is C1-10 alkylene;

$B_b$ is

—$NR_{2b}COR_{3b}$,

—$NR_{2b}CONR_{3b}R_{4b}$,

—$NR_{2b}SO_2R_{3b}$,

—NR$_{2b}$SO$_2$NR$_{3b}$R$_{4b}$ or
—NR$_{2b}$COOR$_{5b}$;

R$_{2b}$, R$_{3b}$, R$_{4b}$ and R$_{5b}$ are independently hydrogen, alkyl, alkoxyalkyl, alkoxyaryl, cycloalkyl, alkenyl, alkynyl, aryl, heteroaryl or aralkyl, with the proviso that when B$_b$ is —NR$_{2b}$SO$_2$R$_{3b}$ or —NR$_{2b}$COOR$_{5b}$, R$_{3b}$ and R$_{5b}$ are not hydrogen and that R$_{3b}$ and R$_{4b}$, taken together with a nitrogen, may form a 5-7 membered hetero ring, are disclosed.

PURPOSE OF THE INVENTION

However, it is difficult to say that the compounds of the formulae (A) and (B) aforementioned are adequate for a practical use at the points of (1) blocking effect on $\beta_1$-receptor, (2) selectivity for $\beta_1$-receptor and (3) short-duration.

Accordingly, the purpose of the present invention is to provide an ideal $\beta_1$-blocker fully satisfying the terms (1) to (3) aforementioned.

The present inventors paid attention to the compounds of the formula (B) aforementioned and have found that the purpose is accomplished by replacing the ester moiety (R$_{1b}$) in the formula (B) by an oxygen-containing heterocyclic ring.

The esterification by an oxygen-containing heterocyclic ring has never been carried out before in the art, and further it is quite unexpected that the duration of $\beta_1$-blocking activity of the compounds of formula (B) grows short by introducing such esters.

SUMMARY OF THE INVENTION

The present invention relates to:
(i) esters of phenylalkanoic acid of the formula:

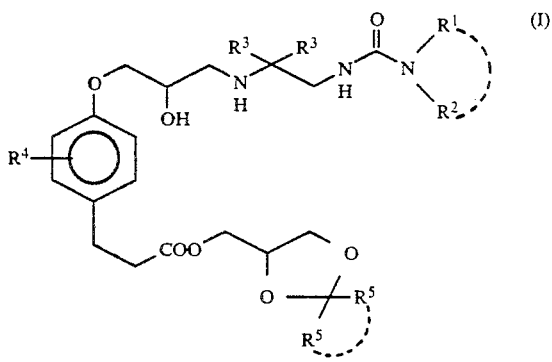

wherein
R$^1$ is 4-10 membered, saturated or unsaturated, mono-or bi-cyclic hetero ring containing as hetero atoms:
(i) one or two nitrogen,
(ii) two or three of nitrogen and sulfur in total, or
(iii) one or two sulfur;
R$^2$ is hydrogen; or
R$^1$ and R$^2$, taken together with a nitrogen to which they are attached, form 4-7 membered, saturated or unsaturated, mono-cyclic hetero ring containing as hetero atoms:
(i) one or two nitrogen, or
(ii) two or three of nitrogen and oxygen in total, the aforementioned hetero rings, represented by R$^1$ or formed by R$^1$ and R$^2$, taken together with a nitrogen to which they are attached, may be substituted by one substituent selected from C1-4 alkyl and C2-5 acyl;

R$^3$ each, independently, is hydrogen or C1-4 alkyl;
R$^4$ is hydrogen, halogen, trihalomethyl, C1-4 alkyl, C1-4 alkoxy, C2-5 acyl, cyano, nitro or nitroxy;
R$^5$ each, independently, is hydrogen, C1-4 alkyl or phenyl; or the two R$^5$'s, taken together with a carbon to which they are attached, form cyclopentane or cyclohexane;
and the pharmaceutically acceptable acid addition salts thereof,
(ii) processes for the preparation thereof and
(iii) $\beta_1$-adrenergic receptor blocking agents containing them as active ingredient.

DETAILED DESCRIPTION OF THE INVENTION

In the formula (I), examples of 4-10 membered, saturated or unsaturated, mono- or bi-cyclic hetero ring containing one or two nitrogen, represented by R$^1$, are pyrrole, imidazole, pyrazole, pyridine, pyridazine, pyrimidine, pyrazine, indole, isoindole, indolidine, quinoline, isoquinoline, quinolizine, indazole, quinazoline, cinnolin, quinoxaline, phthalazin, benzimidazole, and partially or fully saturated rings thereof, and preferably pyridine.

In the formula (I), examples of 4-10 membered, saturated or unsaturated, mono- or bi-cyclic hetero ring containing two or three of nitrogen and sulfur in total, represented by R$^1$, are thiazole, isothiazole, thiadiazoline, benzothiazole, and partially or fully saturated rings thereof.

In the formula (I), examples of 4-10 membered, saturated or unsaturated, mono- or bi-cyclic hetero ring containing one or two sulfur, represented by R$^1$, are thiophen, benzothiophen, 1,4-dithianaphthalene, and partially or fully saturated rings thereof.

In the formula (I), examples of 4-7 membered, saturated or unsaturated, mono-cyclic hetero ring containing one or two nitrogen, formed by R$^1$ and R$^2$, taken together with a nitrogen to which they are attached, are pyrrole, imidazole, pyrazol, pyridine, pyridazine, pyrimidine, pyrazine, and partially or fully saturated rings thereof, for example, piperazine, and preferably piperazine.

In the formula (I), examples of 4-7 membered, saturated or unsaturated, mono-cyclic hetero ring containing two or three of nitrogen and oxygen in total, formed by R$^1$ and R$^2$, taken together with a nitrogen to which they are attached, are oxazole, isooxazole, furazane, and partially or fully saturated rings thereof, for example, morpholine, and preferably morpholine.

In the formula (I), C1-4 alkyl as the substituents of hetero rings, represented by R$^1$ or formed by R$^1$ and R$^2$, taken together with a nitrogen to which they are attached, means methyl, ethyl, propyl, butyl and the isomers thereof; and C2-5 acyl means acetyl, propionyl, butyryl, valeryl and the isomers thereof.

Such hetero ring unsubstituted is also preferred.

In the formula (I), C1-4 alkyl represented by R$^3$, R$^4$ and R$^5$, means methyl, ethyl, propyl, butyl and the isomers thereof.

In the formula (I), halogen represented by R$^4$ means fluorine, chlorine, bromine and iodine; trihalomethyl means trifluoromethyl, trichloromethyl, tribromomethyl and triiodomethyl; C1-4 alkoxy means methoxy, ethoxy, propoxy, butoxy and the isomers thereof; and C2-5 acyl means acetyl, propionyl, butyryl, valeryl and the isomers thereof.

The present invention includes all isomers unless otherwise specified. For example, the alkyl group and alkoxy group mean the straight- or branched-chain alkyl group and alkoxy group. In the case of existing the branched-chain alkyl group, the present invention includes the isomers caused by the existence of the asymmetric carbon atom.

The compounds of the present invention of the formula (I) may be converted into the corresponding acid addition salts by known methods. Preferably, acid addition salts are pharmaceutically acceptable non-toxic salts and water-soluble. Suitable acid addition salts are, for example, an inorganic acid addition salt such as hydrochloride, hydrobromide, sulfate, phosphate, nitrate, or an organic acid addition salt such as acetate, lactate, tartarate, oxalate, fumarate, maleate, citrate, benzoate, methanesulfonate, ethanesulfonate, benzenesulfonate, toluenesulfonate, isethionate, glucuronate, gluconate.

The compounds of the present invention of the formula (I) may be prepared by subjecting to the epoxide-cleaving reaction of a compound of the formula:

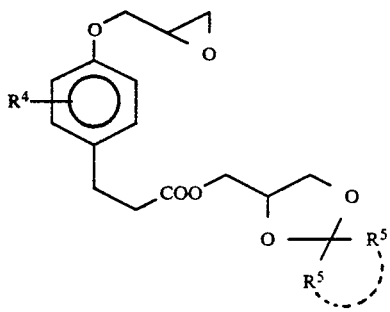

wherein all of the symbols are the same meanings as described hereinbefore, with a compound of the formula:

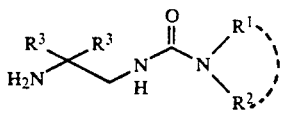

wherein all of the symbols are the same meanings as described hereinbefore.

The epoxide-cleaving reaction is well known per se and may be carried out in an inert organic solvent (diethyl ether, ethanol, isopropyl alcohol, tetrahydrofuran (THF), acetonitrile, N,N'-dimethylformamide (DMF), etc.), at a temperature from ambient to 50° C.

The compounds of the formula (II) may be prepared, for example, by subjecting to a series of reactions depicted in the following Scheme (A).

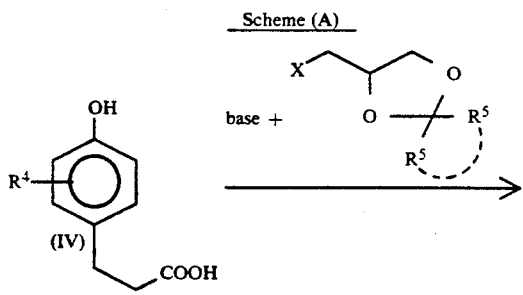

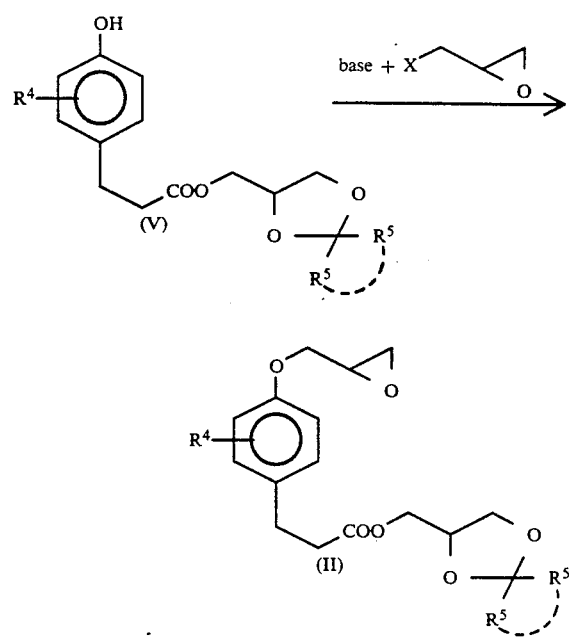

wherein X is halogen, toxyloxy or mesyloxy, and the other symbols are the same meanings as described hereinbefore.

The compounds of the formula (III) may be prepared by subjecting to a reaction depicted in the following Scheme (B).

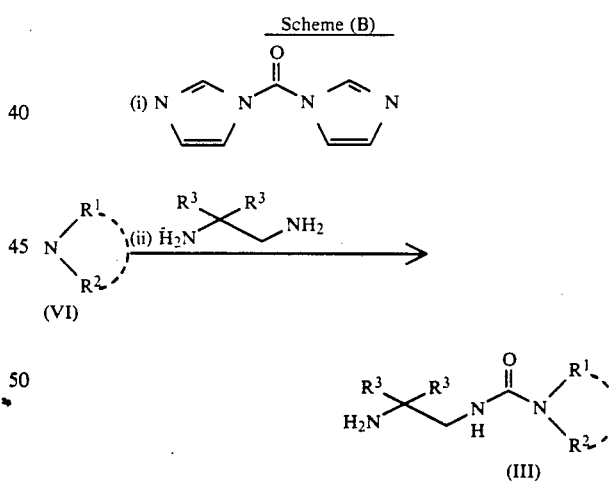

wherein all of the symbols are the same meanings as described hereinbefore.

The starting materials and each reagent used for the preparation in the present invention are known per se, or may be prepared easily by the known methods per se. For example, 3-(4-hydroxyphenyl)propionic acid is on the market.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Pharmacological effect

The $\beta_1$-receptor blocking effect of the compounds of the present invention has been confirmed by the following screening system.

$\beta$-blocking activity of the compounds of the present invention in vivo

Methods

Dogs were anesthetized with sodium barbital (300 mg/kg, ip). A femoral artery and both femoral veins were cannulated. Blood pressure was measured with a pressure transducer. Heart rate was measured from the blood pressure signal using a cardiotachometer. The $\beta$-blocking activity was assessed by the inhibition of isoproterenol-induced tachycardia. Isoproterenol was administered intravenously (0.1~0.3 µg/kg) at 10 minutes intervals. When a regular tachycardia induced by isoproterenol was given, the compound of the present invention was administered (10 µg/kg/min, iv infusion) for 30 minutes. Isoproterenol was given repeatedly during and following infusion of a test compound. The inhibitory effects of the compounds of the present invention on tachycardia were calculated. The results were shown in the following Table I.

Inhibition (%) = (($\Delta RO - \Delta Ra$)/$\Delta RO$) × 100

$\Delta RO$: the increment of heart rate by isoproterenol before infusion of the compound of the present invention $\Delta Ra$: the increment of heart rate by isoproterenol during and after infusion of the compound of the present invention ent invention were calculated. The results were shown in the following Table II.

TABLE II

| Example No. | pA₂ value | | Cardio selectivity $K_B$ (trachea)/ $K_B$ (right atria) |
|---|---|---|---|
| | right atria | trachea | |
| 2 (b) | 6.59 | 4.18 | 255 |

Consideration

As shown in Table I and II aforementioned, it is understood that the compounds of the present invention of the formula (I) have a short-acting blocking effect selective for $\beta_1$-receptor.

On the other hand, it was confirmed that the toxicity of the compounds of the present invention was very low. For example, the acute toxicity (LD$_{50}$) of the compound in Example 2(b) is 290 mg/kg in intravenous administration in mice. Therefore, the compounds of the present invention may be considered to be sufficiently safe and suitable for pharmaceutical use.

As can be seen from the results of pharmacological experiments aforementioned, the compounds of the present invention of formula (I) have a short-acting blocking effect selective for $\beta_1$-receptor, and therefore are useful for the prevention of and/or in the treatment of cardiovascular diseases, for example, angina pectoris, myocardial infarction, congestive heart failure, hypertension, arrhythmia, etc. in mammals including human beings, especially human beings.

For the purpose above described, the compounds of the present invention of the formula (I), and the pharmaceutically acceptable acid addition salts thereof may be normally administered systemically or partially, usu-

TABLE I

| Example No. | Dose (µg/kg/min) | Inhibitory effect after administration of compounds of the present invention (%) | | | | | | | Duration of action* (min) |
|---|---|---|---|---|---|---|---|---|---|
| | | 10 | 20 | 30 | 35 | 40 | 50 | 60 (min) | |
| 2 (b) | 10 | 62.6 | 63.6 | 60.9 | 38.9 | 24.8 | 3.1 | 1.5 | 8.6 |
| 3 (c) | 10 | 38.3 | 46.9 | 40.4 | 37.0 | 20.1 | −2.6 | −1.3 | 10 |
| 3 (e) | 10 | 49.6 | 58.5 | 63.8 | 45.4 | 32.7 | 10.8 | −3.3 | 10 |
| 3 (j) | 10 | 75.7 | 69.0 | 68.7 | 48.9 | 38.3 | 19.3 | 13.6 | 12 |
| 3 (l) | 10 | 60.2 | 58.6 | 59.8 | 55.6 | 41.8 | 19.6 | 16.3 | 15 |

*Duration of action: The time required to decrease the inhibition percent 30 minutes after the administration of the compound of the present invention to the half of the inhibition percent thereof Cardio selectivity of $\beta$-receptor blocking effect of the compounds of the present invention in vitro Methods Heart and trachea were removed from the stunned guinea pig rapidly, and mounted in Krebs-Henseleit solution (referred to as "Krebs solution" hereafter) cooled with ice. Right atria was removed from the heart and connected to a force transducer adjusting the resting tension to 0.5 g in Krebs solution at 37° C. (The solution was airated with 5% $CO_2$ and 95% $O_2$). Trachea was cut into zigzag strip and connected to a force transducer adjusting the resting tension to 0.5 g in the same manner as the atria. After one hour stabilization, the compound of the present invention or a vehicle was added. After one hour, isoproterenol ($10^{-10}$M to $10^{-4}$M) was added cumulatively. Concentration-response curves to isoproterenol were then obtained. All response were calculated as percent of maximum increase in heart rate (in right atria) or percent of maximum decrease in tension (in trachea). The pA₂ values and the cardio selectivity of the compounds of the presally by oral or parenteral administration, preferably parenteral administration.

The doses to be administered are determined depending upon age, symptom, the desired therapeutic effect, the route of administration, and the duration of the treatment, etc. In the human adult, the doses per hour per kg body weight are generally between about 0.001 mg and about 100 mg by intravenous infusion, preferably between about 0.1 mg and about 10 mg, and the doses per kg body weight per dose are generally between about 0.001 mg and about 10 mg by intravenous administration (one shot), preferably between about 0.01 mg and about 1 mg.

As mentioned above, the doses to be used depend upon various conditions. Therefore, there are cases in which doses lower than the ranges specified above and doses greater than the ranges specified above, may be used.

In administration of the compounds of the present invention, solid compositions, liquid compositions and other compositions are used for oral administration, and injections, medicines for external use and suppositories are used for parental administration. Preferably, injections are used for the administration of the compounds of the present invention.

Injections for parenteral administration include sterile aqueous or non-aqueous solution, suspensions and emulsions.

In such injections, one or more of active compounds are admixed with at least one of inert aqueous diluents (distilled water for injection, physiological salt solution etc.) or inert non-aqueous diluents (propylene glycol, polyethylene glycol, olive oil, ethanol, POLYSOLBATE 80 (registered trade mark) etc.).

Injections may comprise the addition of other than inert diluents, e.g. preserving agents, wetting agents, emulsifying agents, dispersing agents, stabilizing agents (lactose etc.), assisting agents such as assisting agents for dissolving (glutamic acid, aspertic acid etc.).

They may be usually sterilized by filtration (through a bacteria-retaining filter etc.), incorporation of sterilizing agents in the compositions or by irradiation. After sterilizing as described, they also be manufactured in the form of sterile solid compositions, for example, by freeze-drying, and which can be dissolved in sterile water or some other sterile diluents for injection immediately before used.

Solid compositions for oral administration include compressed tablets, pills, capsules, dispersible powders, and granules. Capsules includes both hard capsules and soft capsules.

Liquid compositions for oral administration include pharmaceutically acceptable emulsions, solutions, suspensions, syrups and elixirs, and may contain inert diluents commonly used in the art, such as distilled water or ethanol, etc.

Other compositions for parenteral administration include liquids for external use, and endermic agent, such as ointments, liniment, suppositories for rectal administration, and pessaries which comprise one or more of the active compounds and may be prepared by known methods.

REFERENCE EXAMPLES AND EXAMPLES

The following Reference Examples and Examples illustrate but do not limit the present invention.

The solvents in the parentheses show the eluting or developing solvents and the ratios of the solvents used are by volume in chromatographic separation.

Unless otherwise specified, "IR" were measured by KBr method.

REFERENCE EXAMPLE 1

(2,2-dimethyl-1,3-dioxolan-4-yl)methyl 3-(4-hydroxyphenyl)propionate

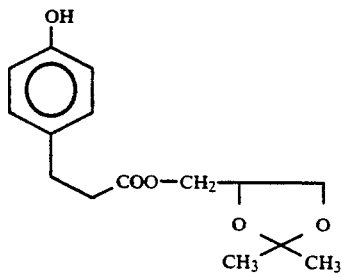

Potassium carbonate (3.8 g) and potassium iodide (7.0 g) were added to a solution of 3-(4-hydroxyphenyl)propionic acid (7.00 g) in dimethyl sulfoxide (25 ml), and the mixture was stirred for 30 minutes at 100° C. under an atmosphere of argon. (2,2-dimethyl-1,3-dioxolan-4-yl)methyl chloride (prepared by the method as described hereinafter; 19.04 g) was added to the mixture, and the mixture was stirred for 15 hours at the same temperature.

The reaction mixture was poured into water (150 ml) and extracted with diethyl ether (150 ml×2). The extract was washed with successive, a saturated aqueous solution of sodium bicarbonate, water and a saturated aqueous solution of sodium chloride, dried over magnesium sulfate and concentrated under reduced pressure. The residue was purified by column chromatography on silica gel(n-hexane: ethyl acetate=2:1) to give the title compound (6.69 g) as white solid having the following physical data.

TLC (n-hexane: ethyl acetate=1:1): Rf=0.54.

(2,2-dimethyl-1,3-dioxolan-4yl)methyl chloride used in the above reaction, was prepared by the following method.

3-chloro-1,2-propanediol (50 g) was dissolved in methylene chloride (100 ml) which was dried over molecular-sieves 3A, and p-toluenesulfonic acid (1.72 g) which was dried by heating, was added to the solution.

The mixture was allowed to cool to 0° C. on ice-bath with stirring under an atmosphere of argon, and 2-methoxypropene (56.2 ml) was added dropwise into the solution over 20 minutes. The reaction mixture was stirred for one hour at room temperature. Triethylamine (2.5 ml) was added dropwise to the reaction solution, and the mixture was concentrated under reduced pressure. The residue was extracted with the mixture of n-hexane and ethyl acetate (10:1), and the extract was washed with successive, water and a saturated aqueous solution of sodium chloride, dried over magnesium sulfate and concentrated under reduced pressure.

The residue was distilled to give (2,2-dimethyl-1,3-dioxolan-4-yl)methyl chloride (52.38 g) having the following physical data. boiling point: 154°–158° C.;

TLC (n-hexane: ethyl acetate=1:1): Rf=0.88.

REFERENCE EXAMPLE 2

(2,2-dimethyl-1,3-dioxolan4-yl)methyl 3-[4-(2,3-epoxypropoxy)-phenyl]propionate

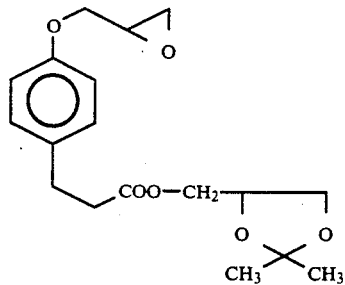

Potassium carbonate (1.406 g) and epibromohydrin (0.58 ml) were added to a solution of the phenol compound (prepared in Reference Example 1;950 mg) in acetone (15 ml), and the mixture was refluxed with stirring for 16 hours.

The reaction mixture was concentrated under reduced pressure, and the residue was dissolved in water (50 ml), and extracted with ethyl acetate. The extract was washed with succesive, water and a saturated aqueous solution of sodium chloride, dried over magnesium sulfate and concentrated under reduced pressure.

The residue was purified by column chromatography on silica gel (ethyl acetate: methylene chloride=4:96) to give the title compound (869 mg) as white solid having the following physical data.

TLC (ethyl acetate: methylene chloride=5:95): RF 0.55.

EXAMPLE 1

(2,2-dimethyl-1,3-dioxolan-4-yl)methyl 3-[4-[2-hydroxy-3-(2-morpholinocarbonylaminoethyl-)aminopropoxy]phenyl]propionate

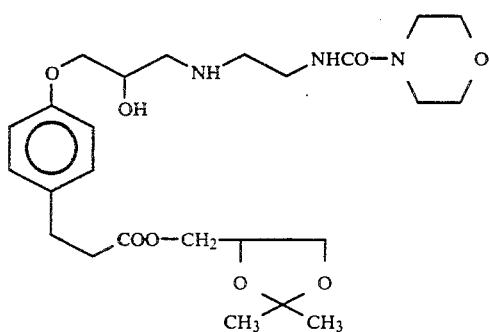

2-(morpholinocarbonylamino)ethylamine (prepared by the method as described hereinafter; 216 mg) was added to a solution of the epoxide compound (prepared in Reference Example 2; 300 mg) in isopropanol (2 ml). Under an atmosphere of argon, the mixture was stirred for 16 hours at 30° C.

The reaction mixture was concentrated under reduced pressure, and the residue was purified by column chromatography on silica gel (ethyl acetate:methanol=4:1) to give the title compound (197 mg) as pale yellow oil having the following physical data.

TLC (methanol): Rf 0.32.

MS: m/z 509(M+), 407, 368, 309, 291, 244, 143, 125, 117, 101.

2-(morpholinocarbonylamino)ethylamine used in the above reaction, was prepared by the following method.

N,N'-carbonyldiimidazole (1.489 g) was dissolved in dry chloroform (8 ml, distilled after the dehydration with calcium hydride), and a solution of morpholine (800 mg) in dry chloroform (2 ml) was added dropwise into the solution with stirring.

The mixture was stirred for 30 minutes at room temperature, and ethylenediamine (2.45 ml) was added dropwise into the reaction solution, and further the mixture was stirred for two days at room temperature.

The reaction mixture was concentrated under reduced pressure, and the residue was purified by column chromatography on silica gel (methanol) to give the title compound (1.49 g) as white solid having the following physical data.

TLC (diethyl ether:ethanol=1:1): Rf 0.11.

EXAMPLE 1 (a)-(b)

The compounds of the present invention shown in the following Table III were obtained by the same procedure as Example 1, by using the optically active epoxide compounds prepared by the same procedures as Reference Example 1 and 2.

TABLE III

| Example No. | Chemical Structure | Name | TLC (Rf) | MS m/z |
|---|---|---|---|---|
| 1 (a) | 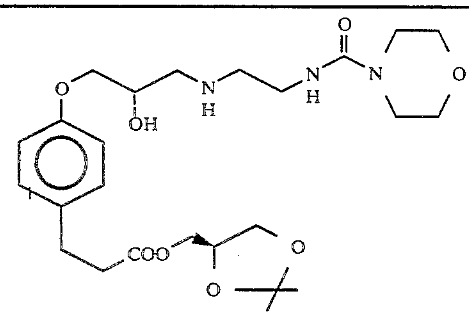 | (2,2-dimethyl-1,3-dioxolan-4R-yl)methyl 3-[4-[2S-hydroxy-3-(2-morpholinocarbonylaminoethyl)aminopropoxy]phenyl]propionate | 0.15 (methanol:methylene chloride = 1:4) | 407, 329, 244, 143, 125, 99 |
| 1 (b) | 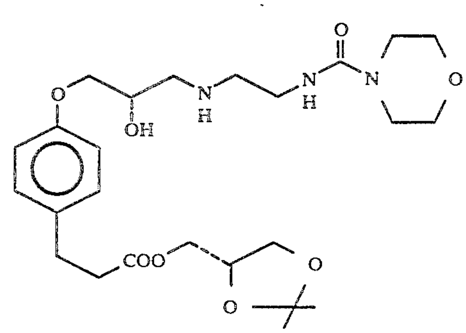 | (2,2-dimethyl-1,3-dioxolan-4S-yl)methyl 3-[4-[2S-hydroxy-3-(2-morpholinocarbonylaminoethyl)aminopropoxy]phenyl]propionate | 0.15 (methanol:methylene chloride = 1:4) | 407, 329, 244, 143, 125, 99 |

EXAMPLE 2

(2,2-dimethyl-1,3-dioxolan-4yl)methyl 3-[4-[2-hydroxy-3-(2-morpholinocarbonylaminoethyl-)aminopropoxy]phenyl]propionate ½ oxalate

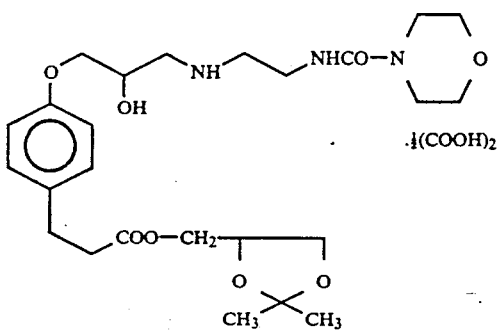

A solution of the amine compound (prepared in Example 1; 197 mg) in chloroform (one ml) was added dropwise to a solution of oxalic acid in diethyl ether (0.1N, 3.87 ml) with stirring, and then the solvent was evaporated away. The obtained solid was dried under reduced pressure overnight to give the title compound (190 mg) as pale orange crystal having the following physical data.

MS: m/z 422, 407, 346, 329, 309, 291, 244, 143, 125, 99;

IR: $\nu$ 3352, 2954, 2857, 1734, 1616, 1542, 1514, 1438, 1307, 1259, 1119, 1044, 827, 768, 721.

EXAMPLE 2 (a)–(d)

The compounds of the present invention shown in the following Table IV were obtained by the same procedure as Example 2, by using the compounds prepared in Example 1(a)–(b) and the various acids.

TABLE IV

| Example No. | Chemical Structure | Name | TLC (Rf) | MS m/z |
|---|---|---|---|---|
| 2 (a) | 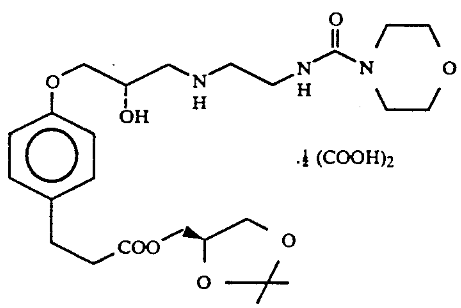 | (2,2-dimethyl-1,3-dioxolan-4R-yl)methyl 3-[4-[2S-hydroxy-3-(2-morpholinocarbonyl-aminoethyl)amino-propoxy]phenyl]-propionate ½ oxalate | 0.15 (methanol:methylene chloride = 1:4) | 407, 329, 244, 143, 125, 99 |
| 2 (b) | 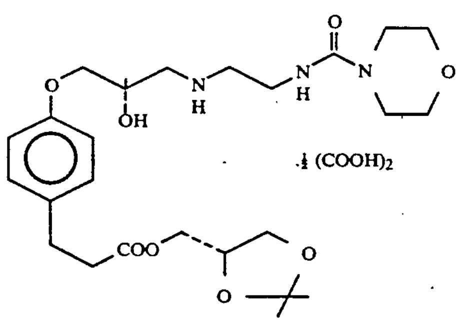 | (2,2-dimethyl-1,3-dioxolan-4S-yl)methyl 3-[4-[2S-hydroxy-3-(2-morpholinocarbonyl-aminoethyl)amino-propoxy]phenyl]-propionate ½ oxalate | 0.15 (methanol:methylene chloride = 1:4) | 407, 329, 244, 143, 125, 99 |
| 2 (c) | 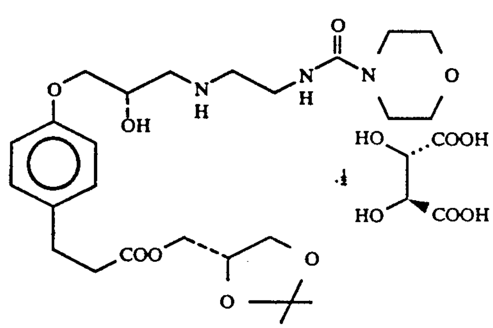 | (2,2-dimethyl-1,3-dioxolan-4S-yl)methyl 3-[4-[2S-hydroxy-3-(2-morpholinocarbonyl-aminoethyl)amino-propoxy]phenyl]-propionate ½ L-(+)-tartarate | 0.153 (ethyl acetate:methanol = 1:1) | 407, 329, 244, 143, 125, 99 |

TABLE IV-continued

| Example No. | Chemical Structure | Name | TLC (Rf) | MS m/z |
|---|---|---|---|---|
| 2 (d) | 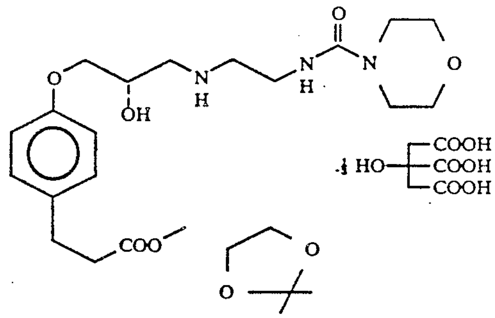 | (2,2-dimethyl-1,3-dioxolan-4S-yl)methyl 3-[4-[2S-hydroxy-3-(2-morpholinocarbonyl-aminoethyl)amino-propoxy]phenyl]-propionate ½ citrate | 0.15 (ethyl acetate:methanol = 1:1) | 407, 329, 244, 143, 125, 99 |

EXAMPLE 3 (a)–(m)

The compounds of the present invention shown in the following Table V were obtained by the same procedure as Example 1 and Example 2, by using the various epoxide compounds and the various 2-(substituted amino)ethylamine, which are prepared by the same procedure as Reference Example 1 and Reference Example 2.

TABLE V

| Example No. | Chemical Structure | Name | TLC (Rf) | MS m/z |
|---|---|---|---|---|
| 3 (a) | 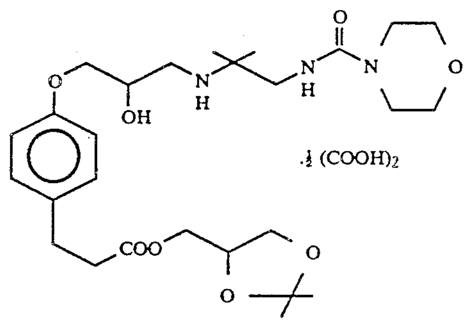 | (2,2-dimethyl-1,3-dioxolan-4-yl)methyl 3-[4-[2-hydroxy-3-(1,1-dimethyl-2-morpholinocarbonyl-aminoethyl)amino-propoxy]phenyl]-propionate ½ oxalate | 0.42 (methanol) | 537, 522, 451, 435, 394, 379, 357, 350, 337, 319, 292, 272, 171, 157, 127, 87, 56 |
| 3 (b) | 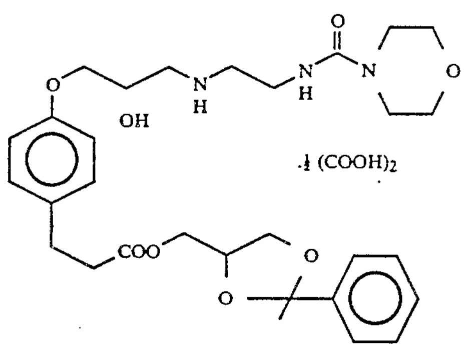 | (2-methyl-2-phenyl-1,3-dioxolan-4-yl)methyl 3-[4-[2S-hydroxy-3-(2-morpholinocarbonyl-aminoethyl)amino-propoxy]phenyl]-propionate ½ oxalate | 0.101 (ethyl acetate:methanol = 1:1) | 572, 157, 143, 114, 99, 86, 70 |
| 3 (c) | 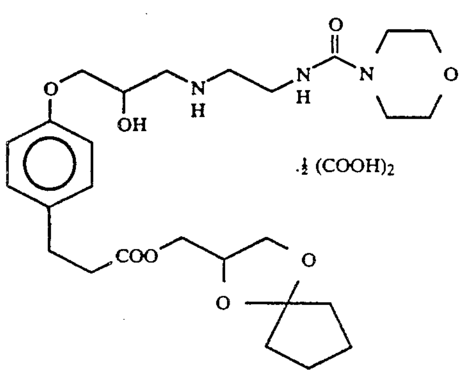 | (1,4-dioxaspiro[4,4]-nonan-2-yl)methyl 3-[4-[2-hydroxy-3-(2-morpholinocarbonyl-aminoethyl)amino-propoxy]phenyl]-propionate ½ oxalate | 0.22 and 0.29 (chloroform:methanol = 8:2) | 448, 430, 419 |

TABLE V-continued

| Example No. | Chemical Structure | Name | TLC (Rf) | MS m/z |
|---|---|---|---|---|
| 3 (d) | (structure) | (2,2-dimethyl-1,3-dioxolan-4-yl)methyl 3-[3-fluoro-4-[2-hydroxy-3-(2-morpholinocarbonyl-aminoethyl)amino-propoxy]phenyl]-propionate ½ oxalate | 0.32 and 0.19 (methanol:methylene chloride = 1:4) | 441, 425, 369, 327, 321, 309, 262, 167, 143, 129, 125, 99 |
| 3 (e) | (structure) | (2,2-dimethyl-1,3-dioxolan-4-yl)methyl 3-[3-fluoro-4-[2S-hydroxy-3-(2-morpholinocarbonyl-aminoethyl)amino-propoxy]phenyl]-propionate ½ oxalate | 0.30 and 0.20 (methanol:methylene chloride = 1:4) | 441, 425, 369, 327, 321, 309, 143, 125, 99 |
| 3 (f) | (structure) | (2,2-dimethyl-1,3-dioxolan-4-yl)methyl 3-[3-fluoro-4-[2R-hydroxy-3-(2-morpholinocarbonyl-aminoethyl)amino-propoxy]phenyl]-propionate ½ oxalate | 0.26 (ethyl acetate:methanol = 1:1) | 425, 420, 368, 327, 309, 262, 236, 167, 143, 125, 99 |
| 3 (g) | (structure) | (2,2-dimethyl-1,3-dioxolan-4-yl)methyl 3-[3-methyl-4-[2S-hydroxy-3-(2-morpholinocarbonyl-aminoethyl)amino-propoxy]phenyl]-propionate ½ oxalate | 0.119 (ethyl acetate:methanol = 1:1) | 436, 421, 305, 258, 163, 143, 125, 99, 91 |
| 3 (h) | (structure) | (2,2-dimethyl-1,3-dioxolan-4-yl)methyl 3-[3-methoxy-4-[2-hydroxy-3-(2-morpholinocarbonyl-aminoethyl)amino-propoxy]phenyl]-propionate ½ oxalate | 0.18 (methanol:methylene chloride = 1:4) | 452, 437, 321, 252, 150, 143, 125, 99 |

TABLE V-continued

| Example No. | Chemical Structure | Name | TLC (Rf) | MS m/z |
|---|---|---|---|---|
| 3 (i) | 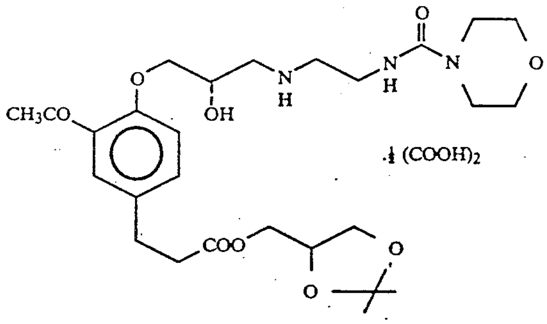 | (2,2-dimethyl-1,3-dioxolan-4-yl)methyl 3-[3-acetyl-4-[2S-hydroxy-3-(2-morpholinocarbonyl-aminoethyl)amino-propoxy]phenyl]-propionate ½ oxalate | 0.123 (ethyl acetate:methanol = 1:1) | 551, 449, 431, 390, 375, 365, 307, 289, 221 |
| 3 (j) | 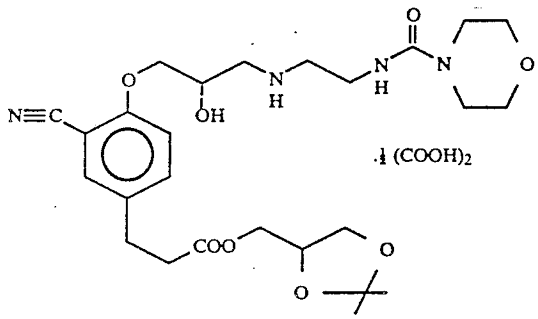 | (2,2-dimethyl-1,3-dioxolan-4-yl)methyl 3-[3-cyano-4-[2S-hydroxy-3-(2-morpholinocarbonyl-aminoethyl)amino-propoxy]phenyl]-propionate ½ oxalate | 0.17 (chloroform:methanol = 6:1) | 535 |
| 3 (k) | 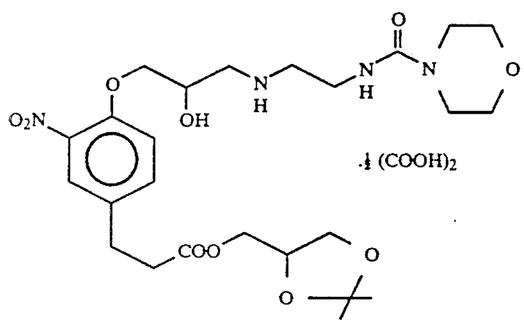 | (2,2-dimethyl-1,3-dioxolan-4-yl)methyl 3-[3-nitro-4-[2-hydroxy-3-(2-morpholinocarbonyl-aminoethyl)amino-propoxy]phenyl]-propionate ½ oxalate | 0.26 (chloroform:methanol = 8:2) | 453, 452, 354, 336, 159, 143, 129 |
| 3 (l) | 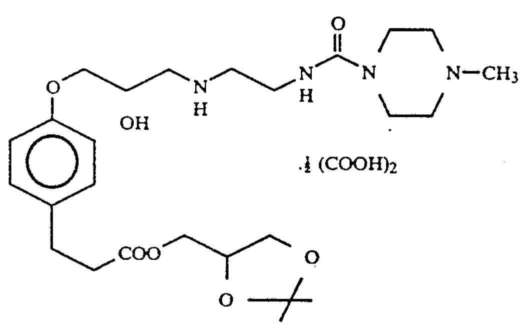 | (2,2-dimethyl-1,3-dioxolan-4-yl)methyl 3-[4-[2S-hydroxy-3-[2-(4-methylpiperazin-1-yl)carbonyl-aminoethyl]amino-propoxy]phenyl]-propionate ½ oxalate | 0.561 (chloroform:methanol:triethylamine = 7:3:2) | 523, 451, 351, 170, 101 |
| 3 (m) | 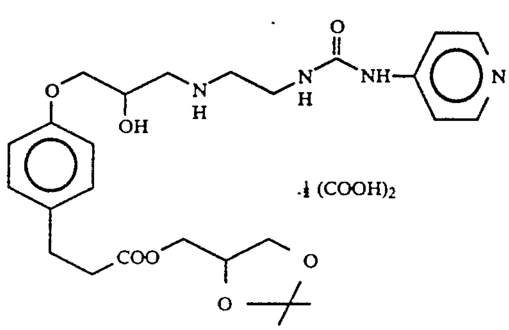 | (2,2-dimethyl-1,3-dioxolan-4-yl)methyl 3-[4-[2-hydroxy-3-[2-(4-pyridyl)amino-carbonyl-aminoethyl]amino-propoxy]phenyl]-propionate ½ oxalate | 0.14 (methanol) | 407, 391, 381, 366, 308, 266, 192, 143, 120, 107, 99, 86 |

FORMULATION EXAMPLE

The following components were admixed in conventional manner. The solution obtained was sterilized in conventional manner, placed in 2 ml portions, in ampoules, and freeze-dried to obtain 100 ampoules each containing 100 mg of the active ingredient for use as intravenous infusion.

(2,2-dimethyl-1,3-dioxolan-4-yl)methyl 3-[4-[2-hydroxy-3-(2-morpholinocarbonylaminoethyl-)aminopropoxy]-phenyl]propionate ½ oxalate — 10 g
maltose — 20 g
distilled water for injection — 200 ml.

What we claim is:

1. An ester of phenylalkanoic acid of the formula:

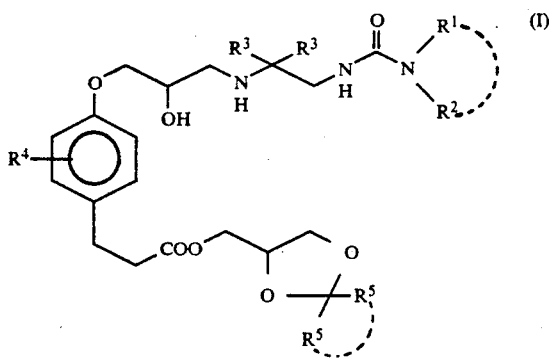

wherein
$R^1$ is 4–10 membered, saturated or unsaturated, mono- or bi-cyclic hetero ring containing as hetero atoms:
  (i) one or two nitrogen,
  (ii) two or three of nitrogen and sulfur in total, or
  (iii) one or two sulfur;
$R^2$ is hydrogen; or
$R^1$ and $R^2$, taken together with a nitrogen to which they are attached, form 4–7 membered, saturated or unsaturated, monocyclic hetero ring containing as hetero atoms:
  (i) one or two nitrogen, or
  (ii) two or three of nitrogen and oxygen in total,
the aforementioned hetero rings, represented by $R^1$ or formed by $R^1$ and $R^2$, taken together with a nitrogen to which they are attached, may be substituted by one substituent selected from C1–4 alkyl and C2–5 acyl;
$R^3$ each, independently, is hydrogen or C1–4 alkyl;
$R^4$ is hydrogen, halogen, trihalomethyl, C1–4 alkyl, C1–4 alkoxy, C2–5 acyl, cyano, nitro or nitroxy;
$R^5$ each, independently, is hydrogen, or C1–4 alkyl or phenyl; or the two $R^5$'s, taken together with a carbon to which they are attached, form cyclopentane or cyclohexane;
or the pharmaceutically acceptable acid addition salts thereof.

2. An ester according to claim 1, wherein $R^1$ and $R^2$, taken together with a nitrogen to which they are attached, represent a morpholino group.

3. An ester according to claim 2, which is
(2,2-dimethyl-1,3-dioxolan-4-yl)methyl 3-[4-[2-hydroxy-3-(2-morpholinocarbonylaminoethyl-)aminopropoxy]phenyl]propionate,
(2,2-dimethyl-1,3-dioxolan-4-yl)methyl 3-[4-[2-hydroxy-3-(1,1-dimethyl-2-morpholinocarbonylaminoethyl)aminopropoxy]phenyl]-propionate,
(2-methyl-2-phenyl-1,3-dioxolan-4-yl)methyl 3-[4-[2-hydroxy-3-(2-morpholinocarbonylaminoethyl-)aminopropoxy]phenyl]propionate,
(1,4-dioxaspiro[4,4]nonan-2-yl)methyl 3-[4-[2-hydroxy-3-(2-morpholinocarbonylaminoethyl-)aminopropoxy]phenyl]propionate,
(2,2-dimethyl-1,3-dioxolan-4-yl)methyl 3-[3-fluoro-4-[2-hydroxy-3-(2-morpholinocarbonylaminoethyl-)aminopropoxy]-phenyl]propionate,
(2,2-dimethyl-1,3-dioxolan-4-yl)methyl 3-[3-methyl-4-[2-hydroxy-3-(2-morpholinocarbonylaminoethyl)aminopropoxy]-phenyl]propionate,
(2,2-dimethyl-1,3-dioxolan-4-yl)methyl 3-[3-methoxy-4-[2-hydroxy-3-(2-morpholinocarbonylaminoethyl)aminopropoxy]-phenyl]propionate,
(2,2-dimethyl-1,3-dioxolan-4-yl)methyl 3-[3-acetyl-4-[2-hydroxy-3-(2-morpholinocarbonylaminoethyl-)aminopropoxy]-phenyl]propionate,
(2,2-dimethyl-1,3-dioxolan-4-yl)methyl 3-[3-cyano-4-[2-hydroxy-3-(2-morpholinocarbonylaminoethyl-)aminopropoxy]phenyl]-propionate or
(2,2-dimethyl-1,3-dioxolan-4-yl)methyl 3-[3-nitro-4-[2-hydroxy-3-(2-morpholinocarbonylaminoethyl-)aminopropoxy]phenyl]-propionate.

4. An ester according to claim 1, wherein $R^1$ and $R^2$, taken together with a nitrogen to which they are attached, represent a piperazinyl.

5. An ester according to claim 4, which is (2,2-dimethyl-1,3-dioxolan-4-yl)methyl 3-[4-[2-hydroxy-3-[2-(4-methylpiperazin-1-yl)carbonylaminoethyl]aminopropoxy]phenyl]-propionate.

6. An ester according to claim 1, wherein $R^1$ is a pyridyl group and $R^2$ is hydrogen.

7. An ester according to claim 6, which is (2,2-dimethyl-1,3-dioxolan-4-yl)methyl 3-[4-[2-hydroxy-3-[2-(4-pyridyl)aminocarbonylaminoethyl]aminopropoxy]phenyl]propionate.

8. A pharmaceutical composition for the prevention of and in the treatment of cardiovascular diseases such as angina pectoris, myocardial infarction, congestive heart failure, hypertension, arrhythmia, which comprises, as active ingredient, an effective amount of an ester of phenylalkanoic acid of the formula (I) depicted in claim 1. or the pharmaceutically acceptable acid addition salt thereof, with a pharmaceutical carrier or coating.

9. A method for the prevention of and in the treatment of cardiovascular diseases such as angina pectoris, myocardial infarction, congestive heart failure, hypertension, arrhythmia, which comprise the administration of an effective amount of an ester of phenylalkanoic acid of the formula (I) depicted in claim 1. or the pharmaceutically acceptable acid addition salt thereof.

* * * * *

UNITED STATES PATENT AND TRADEMARK OFFICE
CERTIFICATE OF CORRECTION

PATENT NO. : 5,013,734

DATED : May 7, 1991

INVENTOR(S) : Sadahiko Iguchi; Masanori Kawamura; Tsumoru Miyamoto

It is certified that error appears in the above-identified patent and that said Letters Patent is hereby corrected as shown below:

Column 21, delete lines 33-38 (beginning with "R¹" and ending with "sulfur;"), and insert the following -- R¹ is a pyridyl group; --;

delete lines 41-50 (beginning with "they are" and ending with "acyl;"), and insert the following -- they are attached, form a morpholino or 4-methylpiperazinyl group --.

Column 22, line 36, after "represent a" insert -- 4-methyl --.

Signed and Sealed this

Fourth Day of May, 1993

Attest:

MICHAEL K. KIRK

*Attesting Officer*   *Acting Commissioner of Patents and Trademarks*